(12) United States Patent
Frank (10) Patent No.: US 8,231,611 B2
(45) Date of Patent: Jul. 31, 2012

(54) SHAFT ROTATING DEVICE (75) Inventor: Timothy Graham Frank, Scotland (GB)

(73) Assignee: University of Dundee (GB)

( * ) Notice: Subject to any disclaimer, the term of this patent is extended or adjusted under 35 U.S.C. 154(b) by 828 days.

(21) Appl. No.: 12/348,119

(22) Filed: Jan. 2, 2009

(65) Prior Publication Data

US 2009/0177039 A1  Jul. 9, 2009

(30) Foreign Application Priority Data

Jan. 3, 2008 (EP) .................................. 08000033

(51) Int. Cl.
*A61B 17/00* (2006.01)
(52) U.S. Cl. ........................................................ 606/1
(58) Field of Classification Search .................. 606/1
See application file for complete search history.

(56) References Cited

U.S. PATENT DOCUMENTS

| | | | |
|---|---|---|---|
| 5,275,614 A | 1/1994 | Haber et al. | |
| 5,782,800 A | 7/1998 | Yoon | |
| 6,156,050 A * | 12/2000 | Davis et al. | 606/181 |

FOREIGN PATENT DOCUMENTS

WO    97/14458 A    4/1997

OTHER PUBLICATIONS

European Search Report, May 16, 2008, 4 pages.
"Laparoscopy" Karl Storz Endoskope; 5th Edition, Jan. 2005, 2 pages.

* cited by examiner

*Primary Examiner* — Aaron Roane
(74) *Attorney, Agent, or Firm* — St. Onge Steward Johnston & Reens LLC (57) ABSTRACT

A shaft rotating device for rotating a shaft of a medical instrument about its longitudinal axis relative to a handle of the medical instrument comprises an operating element for rotating the shaft. The operating element is arranged at a proximal portion of the shaft and it is in driving connection with the shaft such that the shaft is rotatable relative to the handle against frictional forces. The shaft rotating device further comprises a frictional element with a surface. The surface of the frictional element is in frictional contact with the surface of a counterpart for keeping the shaft and the handle rotationally stationary with respect to each other and movable against the frictional forces. The operating element and the frictional element are in operational connection with respect to one another such that a torque applied to the operating element decreases the frictional forces. The shaft and the frictional element are in operational connection with one another such that a torque applied to a distal portion of the shaft increases the frictional forces.

21 Claims, 7 Drawing Sheets

SHAFT ROTATING DEVICE

CROSS REFERENCE TO RELATED APPLICATION

The present application claims priority of European patent application No. 08 000 033.4 filed on Jan. 3, 2008.

BACKGROUND OF THE INVENTION

The invention relates to a shaft rotating device for rotating a shaft of a medical instrument about its longitudinal axis relative to a handle of the medical instrument.

The invention further relates to a medical instrument for endoscopic surgery, comprising a shaft and a handle, wherein the handle is arranged at a proximal portion of the shaft.

A shaft rotating device is, for example, known from the firm catalogue of Karl Storz GmbH & Co., Tuttlingen, "Karl Storz—Endoskope, Laparoskopie", 5. edition 1/2005, page SCC-INTRO 5B. This brochure shows a handle for the laparoscopy with the product number 33131 or 30131 which comprises the known shaft rotating device.

The medical instrument comprising the known shaft rotating device is used for endoscopic operations in the field of the minimally invasive surgery, during which abnormal tissue of e.g. the appendix, the bladder etc. is removed. The present invention, however, is not limited to a use of the shaft rotating device in such a medical instrument.

The known medical instrument comprises an elongated hollow shaft, at whose proximal portion a handle for operation by the surgeon is arranged. A distal portion of the shaft is introduced into a cavity of a patient during the operation, at which jaws are pivotably arranged for grasping and/or cutting tissue. At least one jaw is in driving connection with the handle via a thin pull/push rod for controlling its grasping and/or cutting capability. At the proximal portion of the shaft a shaft rotating device is arranged, which allows the shaft rotating about its longitudinal axis relative to the handle. Upon rotating the shaft, the position of the jaws relative to the tissue can be adapted in the best way regarding the requirements of the operation.

The proximal portion of the shaft is rotationally fixedly accommodated in an opening of the handle. As an outer diameter of the shaft is slightly larger than an inner diameter of the opening, an outer surface of the shaft and an inner surface of the handle are in frictional contact. The known shaft rotation device further comprises an operating element being rotationally fixed at the shaft. Upon operating the operating element, the surgeon can rotate the shaft relative to the handle by a small angular range against the frictional forces. In turn, when outer forces affect the distal portion of the shaft during the operation, an undesired rotation of the shaft relative to the handle is prevented due to the large frictional forces between the surfaces of the shaft and the handle.

It is a disadvantage of the known shaft rotating device, that large frictional forces are required to fix the shaft rotationally stationary with respect to the handle during the operation. For rotating the shaft relative to the handle, these frictional forces have to be overcome, which requires a large torque applied to the operating element during the shaft of the medical instrument being introduced into the body cavity. This aggravates the handling of the instrument and increases the risk of injuries for the patient during the operation.

Furthermore, it is disadvantageous, that the strength of the torque applied to the operating element depends on the frictional forces between the surfaces of the shaft and the handle. In case of small production variations regarding e.g. the materials and dimensions of the shaft and the handle, a torque with a different strength has to be exerted by the surgeon on the operating element. Therefore using such a medical instrument requires the surgeon not only to be experienced with this medical instrument, but also to adapt himself to a medical instrument with a shaft rotating device having slightly different frictional forces.

Moreover, the known shaft rotating device has the drawback, that rotating the shaft against the frictional forces requires a huge physical effort by the surgeon during the operation. The operation is thus physically exhausting for the surgeon, which increases the possibility of unintentional malpractices of the surgeon.

A further disadvantage of the known shaft rotating device is, that any rotation of the shaft relative to the handle mechanically affects the surfaces of the involved components in terms of polishing them, so that these surfaces turn smooth. As a result, the frictional forces between the shaft and the handle can decrease to an extent that the shaft can rotate in undesired fashion, when small external torques are applied to the shaft.

SUMMARY OF THE INVENTION

Therefore it is an object of the present invention to improve both the shaft rotating device and the medical instrument of the kinds mentioned at the outset, so that the medical instrument can be easily operated by the surgeon during the operation without large physical effort.

According to an aspect of the invention, a shaft rotating device for rotating a shaft of a medical instrument about a longitudinal axis of the shaft relative to a handle of the medical instrument is provided, comprising an operating element for rotating the shaft, which is arranged at a proximal portion of the shaft and which is in driving connection with the shaft such that the shaft is rotatable relative to the handle against frictional forces, a frictional element having a first surface, wherein the first surface of the frictional element is in frictional contact with a second surface of a counterpart for keeping the shaft and the handle rotationally stationary with respect to each other and movable against the frictional forces, the operating element and the frictional element being in operational connection with respect to one another such that a torque applied to the operating element decreases the frictional forces, and the shaft and the frictional element being in operational connection with one another such that a torque applied to a distal portion of the shaft increases the frictional forces.

According to another aspect of the invention, a medical instrument for endoscopic surgery is provided, comprising a shaft having a proximal portion and a longitudinal axis, a handle arranged at the proximal portion of the shaft, a shaft rotating device, the shaft rotating device comprising
  an operating element for rotating the shaft, which is arranged at a proximal portion of the shaft and which is in driving connection with the shaft such that the shaft is rotatable relative to the handle against frictional forces,
  a frictional element having a first surface, wherein the first surface of the frictional element is in frictional contact with a second surface of a counterpart for keeping the shaft and the handle rotationally stationary with respect to each other and movable against the frictional forces,
  the operating element and the frictional element being in operational connection with respect to one another such that a torque applied to the operating element decreases the frictional forces, and the shaft and the frictional element being in operational connection with one another such that a torque applied to a distal portion of the shaft increases the frictional forces.

The shaft rotating device of the medical instrument comprises a frictional element, whose surface is in frictional contact with a surface of a counterpart. This arrangement of the two elements provides the frictional forces, so that the shaft and the handle are rotationally stationary with respect to each other. In addition, when applying a torque to the operating element, the frictional forces are decreased such that the shaft is easily rotatable relative to the handle without increased physical effort. In turn, applying a torque to the distal portion of the shaft results in an increase of the frictional forces such that the shaft and the handle are not rotatable relative to each other. The shaft rotating device is thus based on a very easy mechanism that advantageously provides variable frictional forces regarding the externally applied torques, which enables on the one hand a rotationally fixed arrangement of the shaft and the handle when rotation is not desired and on the other hand a rotation of the shaft relative to the handle without large physical effort, when rotation is desired.

This means in the latter case that the surgeon only needs to exert a small torque on the operating element for rotating the shaft relative to the handle, as the frictional forces are reduced upon operating the operating element.

It is a further advantage of the shaft rotating device according to the invention, that the shaft and the handle are not in direct connection with one another, thereby both elements being not damaged due to abrasion of their surfaces.

In a preferred embodiment of the invention, the frictional forces are, when applying the torque to the distal portion of the shaft, increased in that the surface of the frictional element is pressed on the surface of the counterpart.

This way of locking the shaft relative to the handle is very easy in the sense that no further technical means are required for increasing the frictional forces. Therefore production costs of the shaft rotating device and thus the medical instrument are advantageously lower compared to shaft rotating devices comprising more complicated shaft rotating mechanisms.

In a further preferred embodiment of the invention, the frictional forces are, when applying the torque to the operating element, decreased in that the surface of the frictional element is at least partially released from the surface of the counterpart.

This rotating mechanism advantageously allows a very fast and flexible way to rotate the shaft relative to the handle. In addition, the surgeon does not need to apply a large torque to the operating element in order to rotate the shaft, so that the medical instrument can be used in one-hand-operation.

In a further preferred embodiment of the invention, the shaft rotating device further comprises a rotation transmission element which is in rotationally fixed connection with the frictional element for transmitting the torque applied to the distal portion of the shaft to the frictional element.

Here, the rotation transmission element mediates the torque exerted on the distal portion of the shaft to the frictional element due to the rotationally fixed connection of both components, whereby the frictional forces are increased for locking the shaft relative to the handle. Therefore, the frictional element can be advantageously designed to be very small, as the frictional element has not to be in direct connection with the distal portion of the shaft for applying torque to it.

In a further preferred embodiment of the invention, the rotation transmission element is in rotationally fixed connection with the operating element via the frictional element for transmitting the torque applied to the operating element to the frictional element.

In this context, these three components of the shaft rotation device function together to mediate the torque applied to the operating element to the frictional element, whereby the shaft is rotated relative to the handle. Advantageously, the rotation transmission element accomplishes two different functions, so that further components for the rotating mechanism are obsolete and production costs of the shaft rotating device according to the invention are lower compared to more complicated shaft rotating devices.

In a further preferred embodiment of the invention, the rotation transmission element is, when seen in a radial direction, arranged between the frictional element and the operating element.

Arranging the rotation transmission element in such a way offers an easy way for connecting this element in a rotationally fixed way with both the frictional element and the operating element. In this way, this arrangement of the three components advantageously provides a compact design of the shaft rotating device.

In a further preferred embodiment of the invention, the rotation transmission element is slightly spaced from the frictional element.

The advantage here is that no further frictional forces are provided between the rotation transmission element and the frictional element, which could hamper the movement of the shaft relative to the handle when rotation of the shaft relative to the handle is desired. In addition, a damage of both the rotation transmission element and the frictional element is thus prevented, thereby advantageously saving repairing costs for the shaft rotating device and the medical instrument.

In a further preferred embodiment of the invention, the rotation transmission element is slightly spaced from the operating element.

In this context, no further frictional forces are provided between the surfaces of the rotation transmission element and the operating element, thereby advantageously facilitating the movement of the shaft relative to the handle. Furthermore, a damage of both components is prevented, so that no repairing costs for the rotation trans-mission element are incurred.

In a further preferred embodiment of the invention, the rotation transmission element is rotationally fixed to the shaft.

Arranging the rotation transmission element rotationally fixed to the shaft advantageously provides the constructively easiest way for transferring the torque applied to the distal portion of the shaft to the frictional element which then blocks rotation of the shaft relative to the handle.

In a further preferred embodiment of the invention, the counterpart is rotationally fixed to the handle.

The advantage of this measure is, that this design of the shaft rotating device guarantees the shaft and the handle being movable relative to one another.

In a further preferred embodiment of the invention, the surface of the frictional element circumferentially lies on top of the surface of the counterpart.

This arrangement of the frictional element and the counterpart advantageously enables larger frictional forces compared to an arrangement, where the frictional element is in contact with e.g. only few portions of the counterelement. Thus sufficiently large frictional forces are provided for keeping the shaft rotationally stationary with respect to the handle when rotation is undesired.

In a further preferred embodiment of the invention, the operating element is a rotating wheel.

The advantage here is, that a rotating wheel can be easily grasped by the surgeon. In addition, a rotating wheel advantageously allows a rotation of the shaft relative to the handle by an angular range of 360°.

In a further preferred embodiment of the invention, the frictional element is a first and second torsion spring, which are wound in a counter-rotating way with respect to one another and which are arranged around the surface of the counterpart along the longitudinal axis of the shaft.

Two torsion springs advantageously represent a constructively easy design of the frictional element, where the frictional forces are provided between the inner surface of the two springs and the outer surface of the counterelement. Moreover, this arrangement of the springs with windings transverse to the longitudinal axis of the shaft advantageously offers the possibility to press the springs tightly against the surface of the counterpart and release them from it, respectively. It also provides a stable design of the shaft rotating device, as the frictional element cannot be moved or tilted along the shaft extension.

In a further preferred embodiment of the invention, the rotation transmission element is a slotted tube comprising slits, wherein first and second end portions of the first and second springs outwardly extend in an essentially radial fashion and engage into the slits.

This design of the rotation transmission element and the frictional element advantageously provides the rotationally fixed connection of both components, as any rotation of the transmission element is directly transferred to the frictional element via a leverage effect of the first and second end portions of the first and second springs on the slotted tube.

In a further preferred embodiment of the invention, the first end portions of the first and second springs being opposite to one another are arranged next to one another and accommodated within a first slit of the slotted tube.

In this context, the two springs are arranged in such a way that the first end portions of the first and second springs are adjacent to one another. The rotationally fixed connection of the frictional element and the rotation transmission element, i.e. of the first and second springs and the slotted tube, is achieved by the first end portions of the first and second springs engaging into the first slit. When applying a torque to the distal portion of the shaft, a side wall of the first slit presses against the first end portion of that spring which is wounded against the rotational sense of the applied torque, in order to press the surface of this spring closer to the surface of the counterpart. This mechanism advantageously enables locking the shaft relative to the handle independently of the rotational sense of the applied torque.

In a further preferred embodiment of the invention, the rotating wheel comprises recesses for accommodating the second end portions of the first and second springs.

This design of the shaft rotating device causes the second end portions of the first and second springs to engage into the recesses of the rotating wheel for creating the rotationally fixed connection of the frictional element, the rotation transmission element and the rotating wheel. When applying a torque to the rotating wheel, the side wall of the second or third slits presses against the second end portion of that spring being wound in the rotational sense of the applied torque for releasing the surface of this spring from the surface of the counterpart. In this way, the shaft is advantageously rotatable relative to the handle in both direction senses when rotation is desired.

In a further preferred embodiment of the invention, the first end portions of the first and second springs do not have play in the first slit.

In this context, this arrangement of the first end portions of the first and second springs in the first slit of the slotted tube causes the surface of that spring whose first end portion is pressed against to be immediately pressed tighter against the surface of the counterpart. This leads to a direct transfer of the torque applied to the distal portion of the shaft to the frictional element, thereby advantageously preventing any rotation of the shaft relative to the handle even by a small angular range when rotation of the shaft relative to the handle is undesired.

In a further preferred embodiment of the invention, the second end portions of the first and second springs have play in second and third slits of the slotted tube.

The advantage of this measure is, that an unintentional rotation of the operating element does not immediately result in a rotation of the shaft relative to the handle.

In a further preferred embodiment of the invention, the first and second springs comprise at least two turns.

Designing the springs with at least two turns advantageously provides enough contact surface of the first and second springs, i.e. of the frictional element, with respect to the surface of the counterpart for creating sufficiently large frictional forces. In addition, tilting of the first and second springs towards the longitudinal extension of the shaft is prevented, as two circumferentially windings of the springs form a very stable arrangement.

In a further preferred embodiment of the invention, an inner diameter of the first and second springs is by approximately 0.5% to 2.0%, preferably by approximately 1%, smaller than an outer diameter of the counterpart.

In this context, these diameters of both components evoke the frictional forces between the involved surfaces, as the first and second springs tightly fit on the outer surface of the counterpart. Therefore any relative movement of the shaft and the handle is advantageously prevented.

Further advantages will be apparent from the following description and the accompanying drawings. It is to be understood that the afore-mentioned features and those to be explained below are not only applicable in the combinations given, but also in other combinations or in isolation without departing from the scope of the invention.

BRIEF DESCRIPTION OF THE DRAWINGS

An exemplary embodiment of the invention is illustrated in the drawings and will be described hereinafter with reference thereto. In the drawings.

DETAILED DESCRIPTION OF A PREFERRED EXEMPLARY EMBODIMENT

Figure 1:
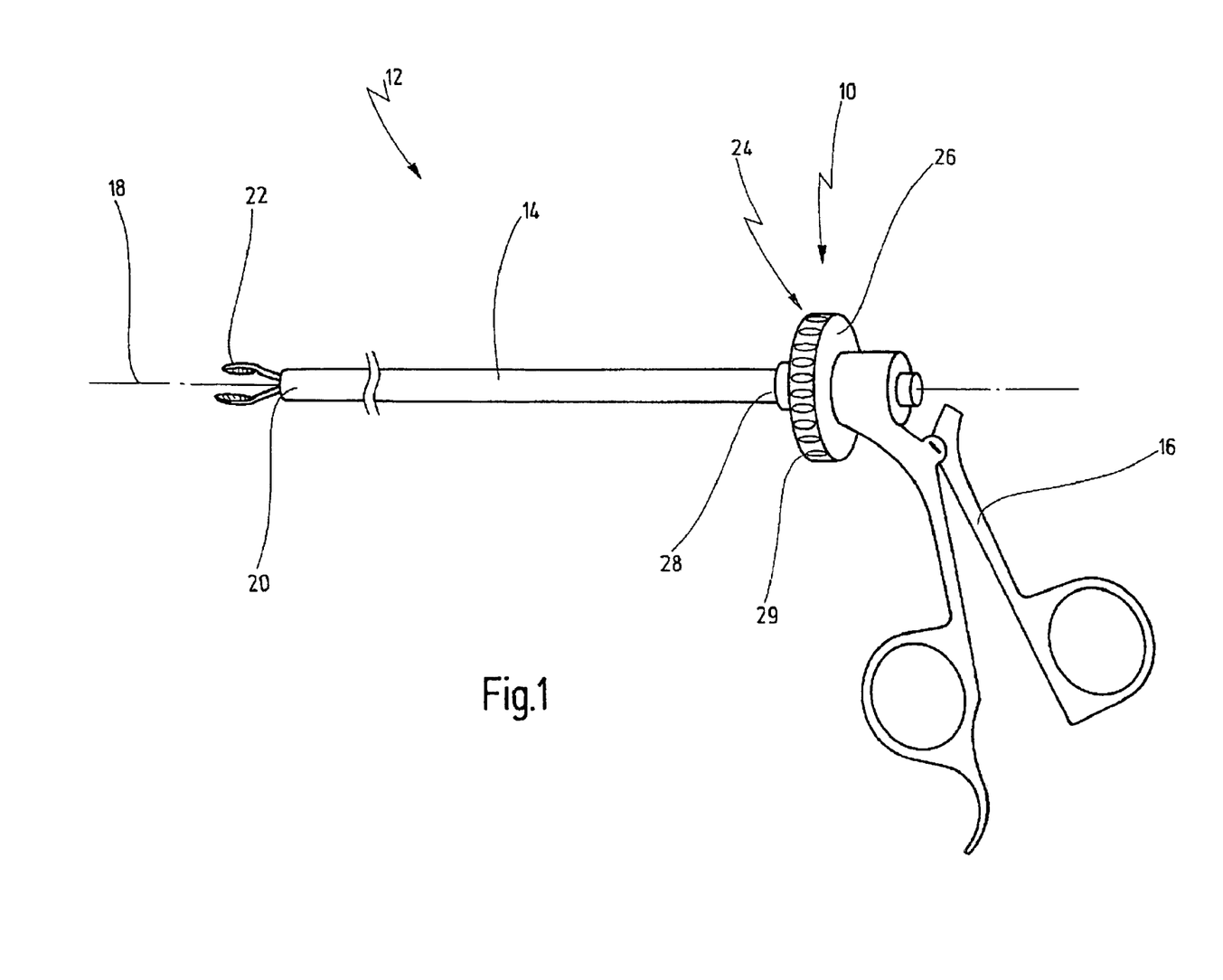
FIG. 1 is a schematic view of a medical instrument comprising a shaft rotating device in accordance with the invention.

FIG. 1 shows, in a schematic representation, a shaft rotating device generally labelled with reference numeral 10 as part of a medical instrument 12. The shaft rotating device 10 is used for rotating an elongated hollow shaft 14 of the medical instrument 12 with respect to a handle 16 of the medical instrument 12 about a longitudinal axis 18 of the shaft 14. Further details of the shaft rotating device 10 are shown in FIGS. 2A through 5.

Preferably, the medical instrument 12 is made of steel to be easily cleaned after being used.

During an operation a distal portion 20 of the shaft 14 is introduced into a body cavity of a patient for e.g. grasping and/or cutting tissue e.g. of the appendix. Jaws 22, which are pivotably arranged at the distal portion 20 of the shaft 14, are connected with the handle 16 via an axially movable force transmission mechanism (not shown) such as a push/pull rod. Upon rotating the shaft 14 relative to the handle 16, the jaws 22 are rotated for arranging them in the most convenient position with respect to the tissue and thus improving their grasping and/or cutting capabilities during the operation.

The shaft rotating device 10 comprises an operating element 24, here a rotating wheel 26, for rotating the shaft 14 relative to the handle 16. The rotating wheel 26 is arranged at a proximal portion 28 of the shaft 14. Moreover, it is in driving connection with the shaft 14 such that the shaft 14 is rotatable relative to the handle 16 against frictional forces. The design of the rotating wheel 26 allows a rotation of the shaft 14 by an angular range of 360° in both rotation senses. For facilitating its usage, the rotating wheel 26 comprises grooves 29 which run in an essentially parallel way with respect to the extension of the shaft 14. The rotating wheel 26 is made of steel. However, it can also be made of a light material such as teflon.

Figure 2A:
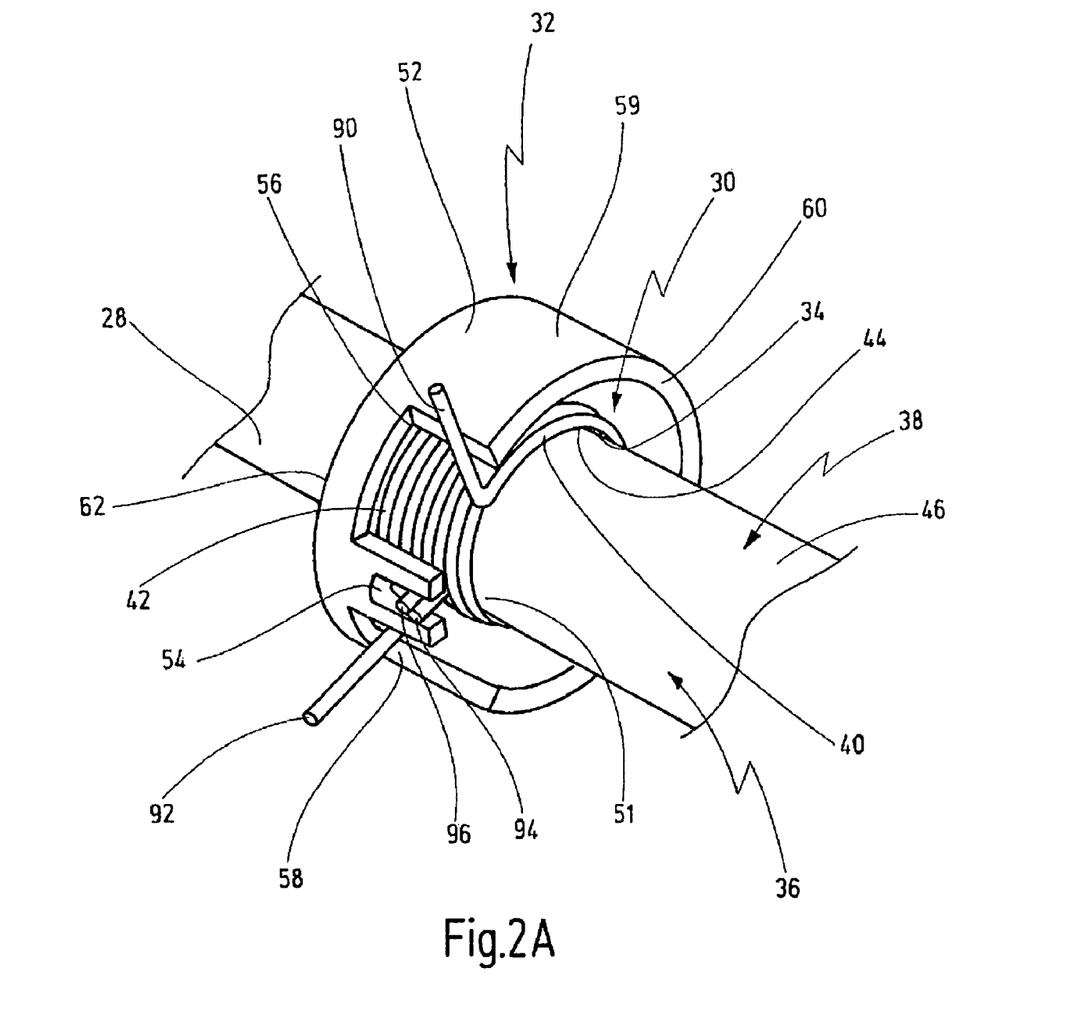
FIG. 2A is a perspective view of a proximal portion of the shaft of the instrument in FIG. 1, at which a slotted tube and first and second springs are arranged.

As shown in FIG. 2A, the shaft rotating device 10 further comprises a frictional element 30 and a rotation transmission element 32.

The frictional element 30 comprises a surface 34 which is in frictional contact with a surface 36 of a counterpart 38 for providing the frictional forces between both components. Here, the counterpart 38 is rotationally fixed to the handle 16. In this way, these frictional forces oppose any movement of the shaft 14 relative to the handle 16 for keeping both the handle 16 and the shaft 14 rotationally stationary with respect to each other.

In addition, the frictional element 30 and the rotating wheel 26 are in operational connection with respect to one another such that a torque externally applied to the rotating wheel 26 by a surgeon decreases the frictional forces between the surfaces 34, 36 of the frictional element 30 and the counterpart 38. In turn, the frictional forces between both components are increased for locking the shaft 14 with respect to the handle 16, when a torque is applied to the distal portion 20 of the shaft 14 during the operation. Such a torque may be caused by the interaction between the jaws 22 and the tissue to be treated. In order to enable the latter effect, the shaft 14 and the frictional element 30 are in operational connection.

The rotation transmission element 32 is rotationally fixed to the proximal portion 28 of the shaft 14. It is further in rotationally fixed connection with the frictional element 30, in order to transmit the torque applied to the distal portion 20 of the shaft 14 to the frictional element 30. A further rotationally fixed connection of the rotation transmission element 32 and the rotating wheel 26 via the frictional element 30 enables mediating the torque applied to the rotating wheel 26 to the frictional element 30. When seen in a radial way, the rotation transmission element 32 is further arranged between the frictional element 30 and the rotating wheel 26 leading to a very compact design of the shaft rotating device 10 (see FIG. 5).

Figure 2B:
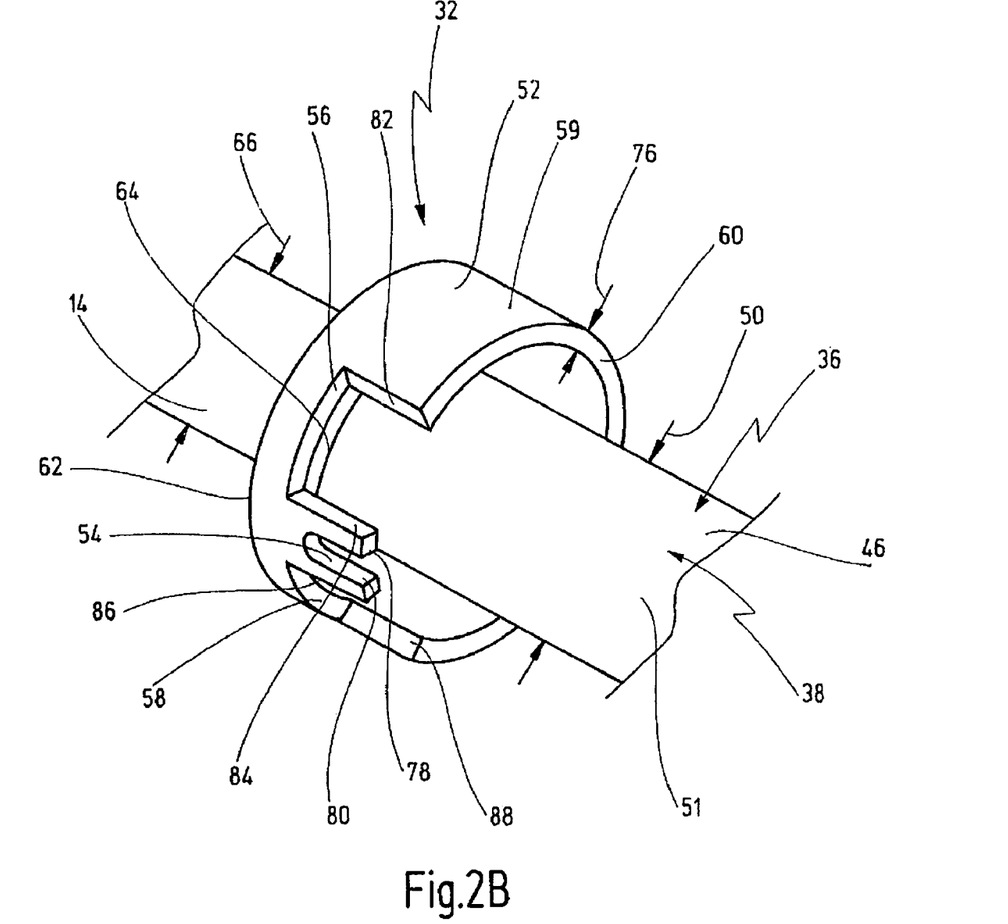
FIG. 2B is a further perspective view of the proximal portion of the shaft in FIG. 2A without the first and second springs.

As shown in FIGS. 2A, 2B, the frictional element 30 is designed as first and second springs 40, 42, whose windings are counter-rotating with respect to one another. The first and second springs 40, 42 are arranged along the longitudinal axis 18 of the shaft 14 in such a way that their windings are transverse with respect to the longitudinal axis 18 of the shaft 14. Thus the surface 34 of the frictional element 30 corresponding to an inner surface 44 of the first and second spring 40, 42 circumferentially lies on top on the surface 36 of the counterpart 38 providing sufficiently large frictional forces for keeping the shaft 14 rotationally stationary with respect to the handle 16.

The first and second springs 40, 42 are identically designed and comprise at least two turns, here exactly two turns. They are made of steel for providing enough rigidity of their rotationally fixed connection to the operating element 24 and the rotation transmission element 32.

Figure 4:
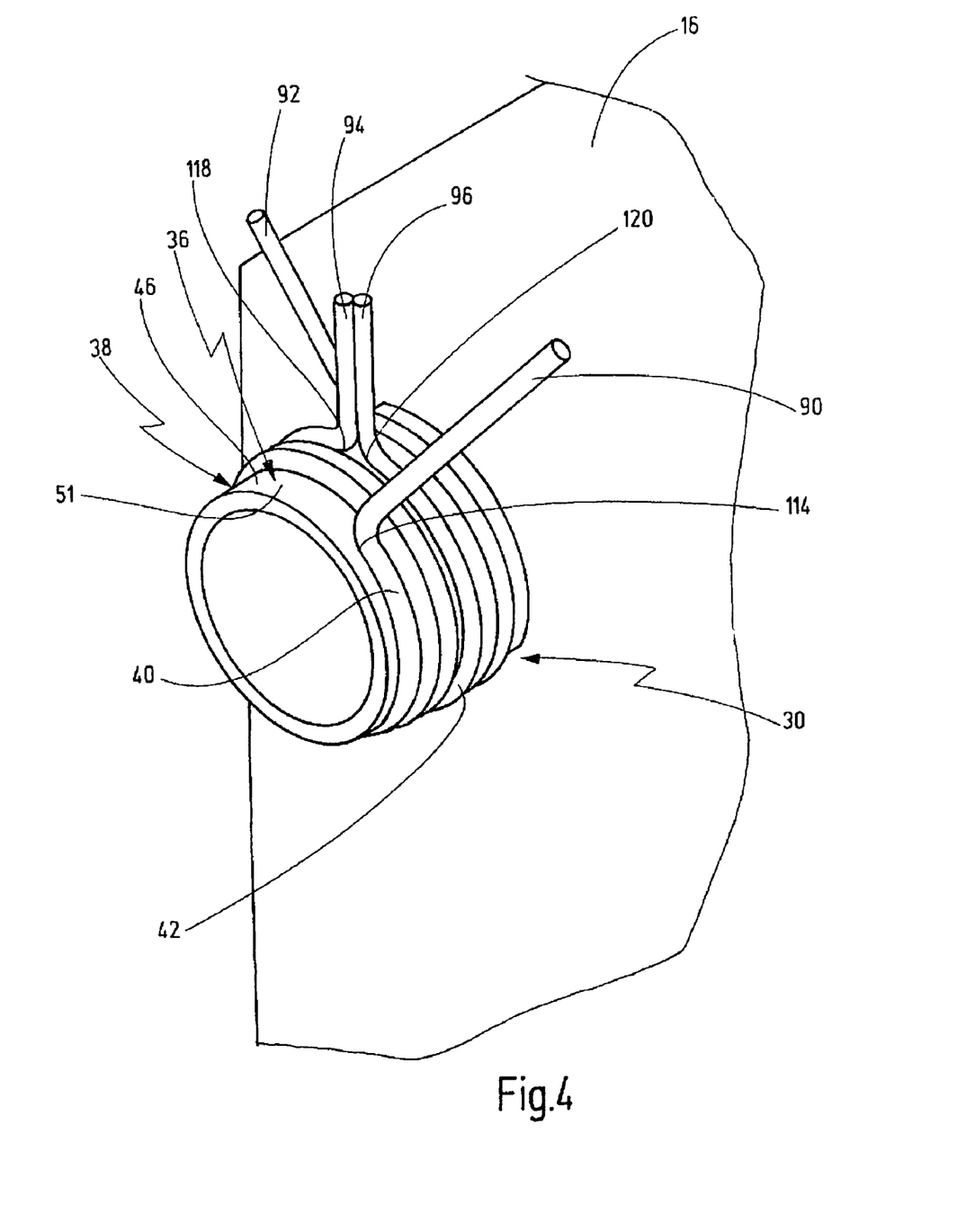
FIG. 4 is a perspective view of the counterpart of the handle, on which the first and second springs in FIG. 3A are arranged.

The counterpart 36 is designed as a collar 46 made of steel which is rotationally fixed to the handle 16. As it is shown in FIG. 4, the collar 46 projects from the handle 16 by an angle of almost 90°, so that a proximal end portion (not shown) of the shaft 14 is rotationally accommodated in the collar 46. The collar 46 and the handle 16 are designed as distinct components, however, both can be also formed in a single-pieced or monolithic way.

For providing the frictional forces, an inner diameter 48 of the first and second springs 40, 42 is by approximately 0.5% to 2.0%, preferably by approximately 1%, smaller than an outer diameter 50 of the collar 46. In this way, the first and second springs 40, 42 fit tightly around a surface 51 of the collar 46, whereby the first and second springs 40, 42 are rigidly held on the surface 51 of the collar 46.

The rotation transmission element 32 is designed as a slotted tube 52, e.g. made of steel which is arranged in an parallel way with respect to the longitudinal axis 18 of the shaft 14. The slotted tube 52 comprises a first, second and third slit 54-58, which are formed within a peripherical wall 59 of the slotted tube 52 in an essentially parallel way with respect the longitudinal axis 18 of the shaft 14. They extend from a first front side 60 being open and arranged near the handle 16 to approximately ⅔ of a tube extension. A second front side 62 is formed ring-like, where an inner diameter of an opening 64 of the second front side 62 approximately coincides with an outer diameter 66 of the shaft 14. In order to rotationally fix the slotted tube 52 to the shaft 14, the ring opening 64 is welded to the shaft 14. However, the shaft 14 and the slotted tube 52 can be also designed in a single-pieced way.

Furthermore, an inner diameter 68 of the slotted tube 52 is slightly larger than an outer diameter 70 of the first and second springs 40, 42, so that the tube 52 is slightly spaced from the first and the second springs 40, 42. In this way, no further frictional forces are provided between both components, which could negatively affect the rotation of the shaft 14 relative to the handle 16 in the sense that further frictional forces are provided which have to be overcome when the surgeon wishes to rotate the shaft. Additionally, an outer diameter 72 of the tube 52 is slightly smaller than an inner diameter 74 of the rotating wheel 26, so that both components are slightly spaced from each other. Therefore, no additional frictional forces are provided between these two components for allowing an easy and flexible operating mechanism of the rotating wheel 26. Depending on the material of the slotted tube 52 a wall thickness 76 of the tube 52 is dimensioned in such a way, that it provides enough rigidity against external forces exerted on it.

Side walls 78, 80 of the first slit 54 are designed in such a way that they run in an almost parallel way respecting each other and the longitudinal axis 18 of the shaft 14. In contrast, the second and third slits 56, 58 broaden towards the first and second springs 40, 44, so that side walls 82-88 of the second and third slits 56, 58 are not parallelly formed to each other.

Figure 3A:
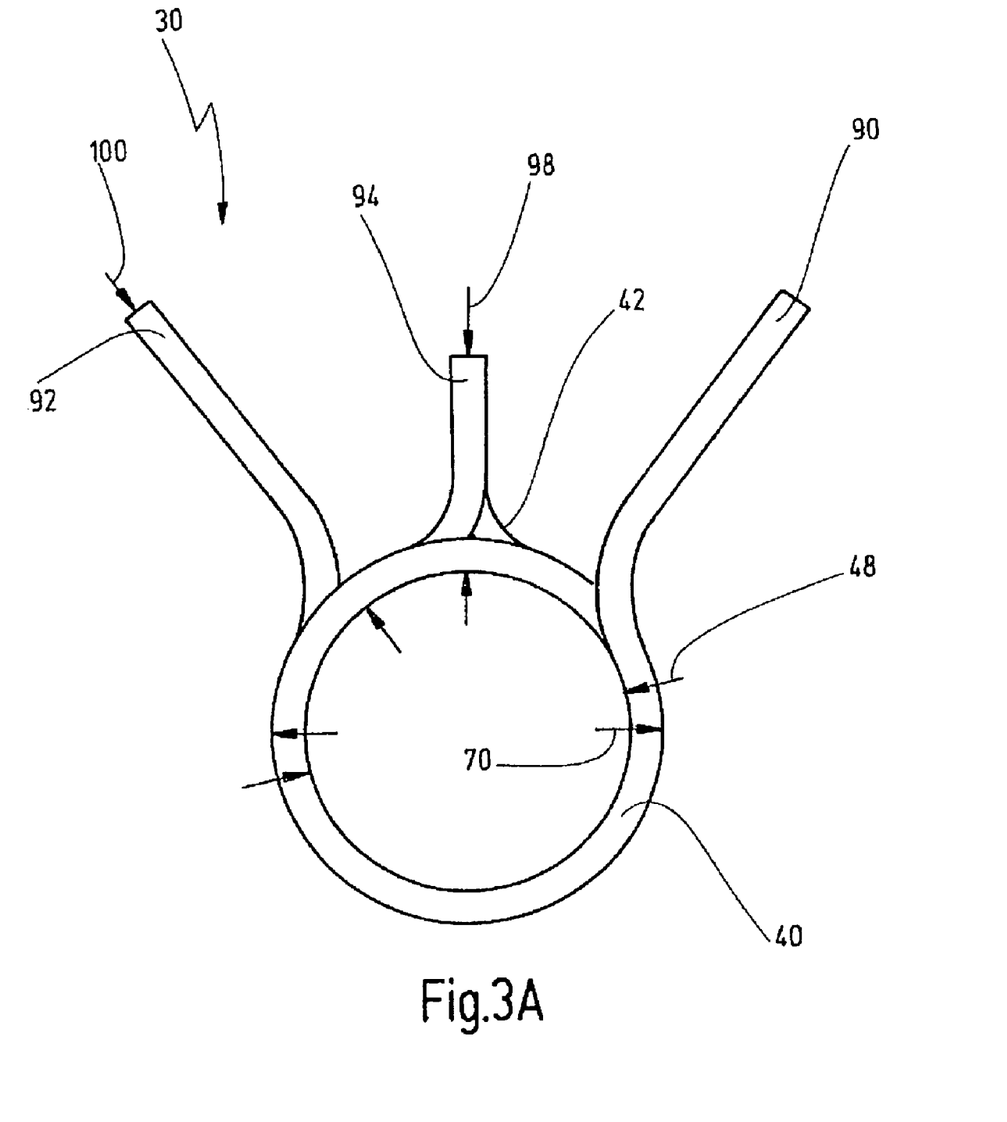
FIG. 3A is a cross sectional view of the first and second springs in FIG. 2A.

The first and second springs 40, 42 comprise first and second end portions 90-96, which outwardly extend in an essentially radial way, so that the first and second end portions 90-96 of the first and second springs 40, 42 engage into the slits 54-58. The opposite first end portions 90, 92 of the first and second springs 40, 42 are arranged directly next to one another, whereas the second end portions 94, 96 of each spring 40, 42 are arranged by an angle of approximately 45° respecting the associated first end portions 90, 92.

Figure 3B:
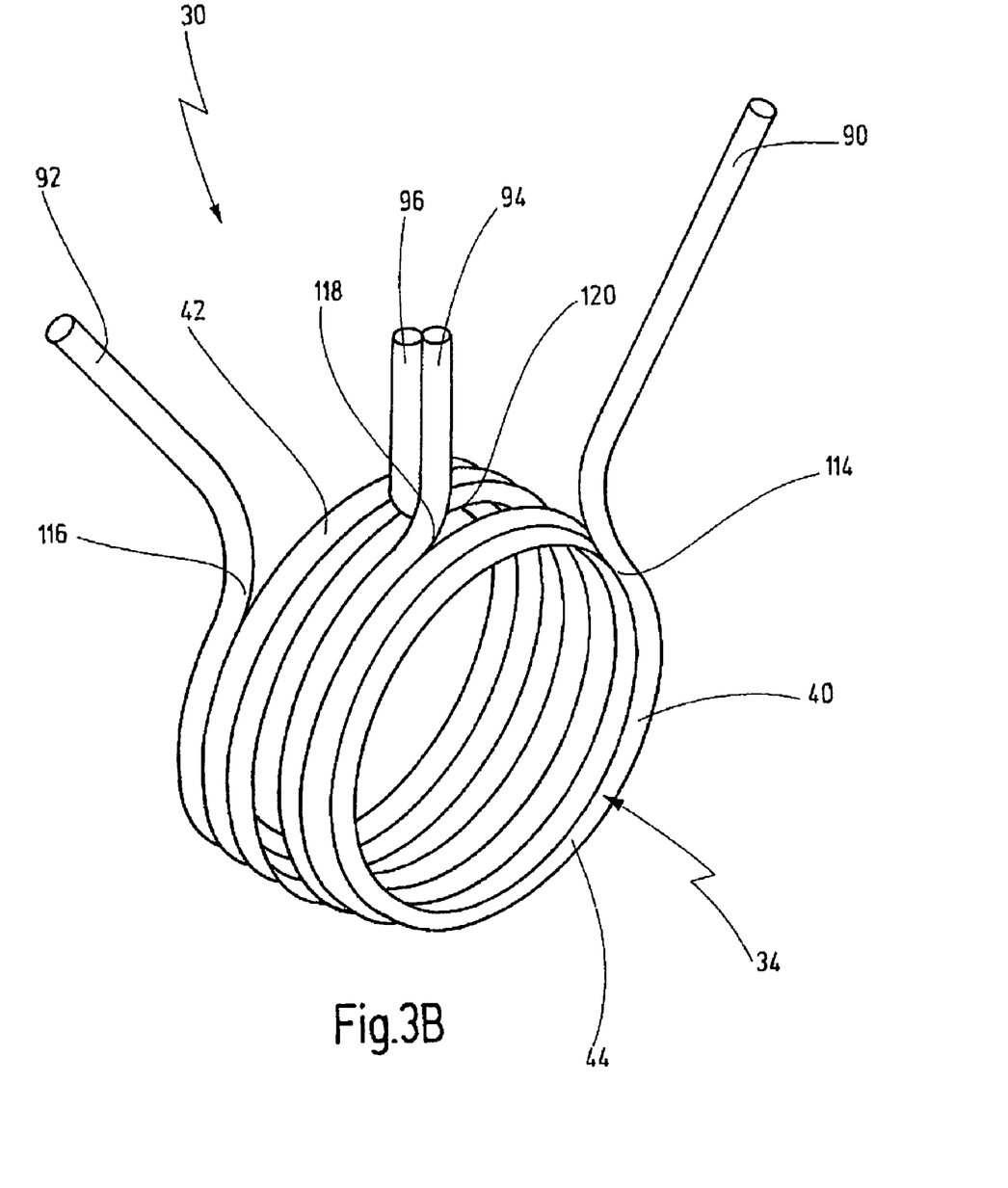
FIG. 3B is a perspective view of the first and second springs in FIG. 3A.

As shown in FIG. 3B, the first and second springs 40, 42 comprise two turns of 360° and one turn of 315°, so that the second end portions 94, 96 are arranged in front of the first end portions 90, 92, when seen in the winding sense of the first and second springs 40, 42. It is also possible, that the first and second springs 40, 42 comprise three turns of 360° and one of 45°, so that the second end portions 94, 96 are arranged behind the first end portions 90, 92, when seen in the winding sense of the first and second springs 40, 42.

A length 98 of the first end portions 90, 92 is smaller than a length 100 of the second end portions 94, 96. Therefore the first end portions 90, 92 are accommodated in the first slit 54 of the slotted tube 52, whereas the longer second end portions 94, 96 extend through the second and third slits 56, 58, respectively.

Figure 5:
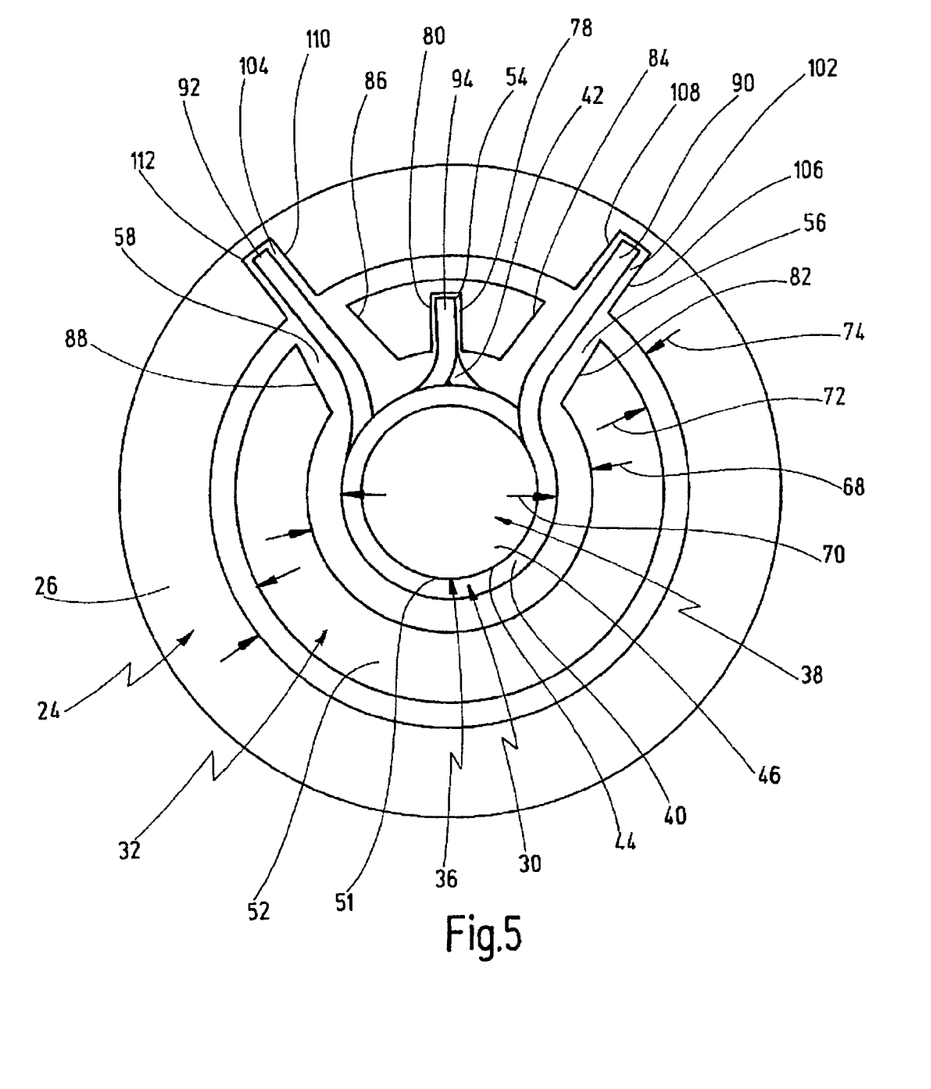
FIG. 5 is a cross sectional view of the rotating wheel, the slotted tube and the first and second springs.

As shown in FIG. 5, the rotating wheel 26 comprises two recesses 102, 104, in which the second end portions 94, 96 of the first and second springs 40, 42 are received.

The first and second end portions 90-96 thus provide the rotationally fixed connection of the slotted tube 52 to the first and second springs 40, 42 and the rotating wheel 26, respectively.

In order to rotate the shaft 14 relative to the handle 16 or to keep both components rotationally stationary with respect to each other, the frictional forces between the first and second springs 40, 42 and the collar 46 are, as mentioned above, variable, i.e. they can be decreased or increased, respectively. The frictional forces are decreased by at least partially releasing the inner surface 44 of the first and second springs 40, 42, i.e. the surface 34 of the frictional elements 30, from the surface 51 of the collar 46, i.e. from the surface 36 of the counterpart 38. In addition, the frictional forces are increased in such a way that the inner surface 44 of the first and second springs 40, 42, i.e. the surface 34 of the frictional elements 30, is pressed onto the surface 51 of the collar 46, i.e. onto the surface 36 of the counterpart 38.

When applying a torque to the rotating wheel 26 in order to rotate the shaft 14, for example clockwise with respect to FIG. 5, side walls 108, 112 of the recesses 102, 104, which are arranged in counter-rotational sense, press against both second end portions 94, 96 of the first and second springs 40, 42. As the second end portions 94, 96 of the first and second springs 40, 42 have play in the second and third slits 56, 58, the rotating wheel 26 is first rotated by a small angular range, until the second end portion 94 of the first spring 40, being wound in the rotational sense of the applied torque, is pressed tighter onto the side wall 82 of the corresponding second slit 56. A portion 114 of the first spring 40 is released from the surface 51 of the collar 46, as the side wall 82 of the corresponding second slit 56 broadens towards the windings of the first and second springs 40, 42. Thus the frictional forces between the first spring 40 and the collar 46 are decreased. The slotted tube 52 and thus the shaft 14 move in the rotation sense of the rotating wheel 26. The second end portion 96 of the second spring 42 being wound in counter-rotational sense does not come into contact with the side wall 88 of the third slit 58, so that a portion 116 of the second spring 42 is not pressed tighter onto the surface 36 of the collar 46, whereby the frictional forces between the second spring 42 and the collar 46 are not increased and the clockwise rotation of the first and second springs 40, 42 is not affected. When changing the rotation sense of the rotating wheel 26, the corresponding function applies.

When a torque is applied to the distal portion 20 of the shaft 14, for example clockwise with respect to FIG. 5, the shaft 14 remains rotationally stationary with respect to the handle 16. As the first end portions 90, 92 of the first and second springs 40, 42 do not have play in the first slit 54, the side wall 80 of the first slit 54 is immediately pressed against both the first end portions 90, 92 of the first end second springs 40, 42. The parallel shape of the side walls 78, 80 causes a portion 118 of first spring 40 to be pressed tighter onto the surface 51 of the collar 46, whereas a portion 120 of the second spring 42 is not released from the surface 51 of the collar 46. Furthermore, the second end portions 94, 96 of the first and second springs 40, 42 do not come into contact with the side walls 82-88 of the second and third slits 56, 58, as the second end portions 94, 96 have play in them. Therefore the frictional forces 10 are increased and the shaft 14 is kept rotationally stationary with respect to the handle 16. According to an identical design of the first and second springs 40, 42, the shaft 14 is also unmovable relative to the handle 16 when a torque is applied anticlockwise to the distal portion 20 of the shaft 14.

What is claimed, is:

1. A shaft rotating device for rotating a shaft of a medical instrument about a longitudinal axis of said shaft relative to a handle of said medical instrument, comprising an operating element for rotating said shaft, which is arranged at a proximal portion of said shaft and which is in driving connection with said shaft such that said shaft is rotatable relative to said handle against frictional forces, a frictional element having a first surface, wherein said first surface of said frictional element is in frictional contact with a second surface of a counterpart, rotationally fixed to the handle, for keeping said shaft and said handle rotationally stationary with respect to each other and movable against said frictional forces, said operating element and said frictional element being in operational connection with respect to one another such that a torque applied to said operating element decreases said frictional forces, and said shaft and said frictional element being in operational connection with one another such that a torque applied to a distal portion of said shaft increases said frictional forces.

2. The shaft rotating device of claim 1, wherein, when applying said torque to said distal portion of said shaft, said frictional forces are increased in that said first surface of said frictional element is pressed on said second surface of said counterpart.

3. The shaft rotating device of claim 1, wherein, when applying said torque to said operating element, said frictional forces are decreased in that said first surface of said frictional element is released at least partially from said second surface of said counterpart.

4. The shaft rotating device of claim 1, further comprising a rotation transmission element which is in rotationally fixed connection with said frictional element for transmitting said torque applied to said distal portion of said shaft to said frictional element.

5. The shaft rotating device of claim 4, wherein said rotation transmission element is in rotationally fixed connection with said operating element via said frictional element for transmitting said torque applied to said operating element to said frictional element.

6. The shaft rotating device of claim 4, wherein, when seen in a radial direction, said rotation transmission element is arranged between said frictional element and said operating element.

7. The shaft rotation device of claim 4, wherein said rotation transmission element is slightly spaced from said frictional element.

8. The shaft rotation device of claim 7, wherein said rotation transmission element is slightly spaced from said operating element.

9. The shaft rotation element of claim 4, wherein said rotation transmission element is rotationally fixed to said shaft.

10. The shaft rotating device of claim 4, wherein said rotation transmission element has a slotted tube comprising slits, wherein first and second end portions of said first and second torsion springs outwardly extend in an essentially radial fashion and engage into said slits.

11. The shaft rotating device of claim 10, wherein said first end portions of said first and second torsion springs being opposite to one another are arranged next to one another and accommodated within a first slit of said slits of said slotted tube.

12. The shaft rotating device of claim 11, wherein said operating element is a rotating wheel, and said rotating wheel comprises recesses for accommodating said second end portions of said first and second torsion springs.

13. The shaft rotating device of claim 10, wherein said first end portions of said first and second torsion springs do not have play in a first slit of said slits of said slotted tube.

14. The shaft rotating device of claim 10, wherein said second end portions of said first and second torsion springs have play in second and third slits of said slits of said slotted tube.

15. The shaft rotating device of claim 1, wherein said counterpart is rotationally fixed to said handle.

16. The shaft rotating device of claim 1, wherein said first surface of said frictional element circumferentially lies on top of said second surface of said counterpart.

17. The shaft rotating device of claim 1, wherein said operating element is a rotating wheel.

18. The shaft rotating device of claim 1, wherein said frictional element has a first and a second torsion spring, which are wound in a counter-rotating way with respect to one another and which are arranged around said second surface of said counterpart along a longitudinal axis of said shaft.

19. The shaft rotating device of claim 18, wherein said first and second torsion springs have at least two turns.

20. The shaft rotating device of claim 18, wherein an inner diameter of said first and second torsion springs is by approximately 0.5% to 2.0% smaller than an outer diameter of said counterpart.

21. A medical instrument for endoscopic surgery, comprising a shaft having a proximal portion and a longitudinal axis, a handle arranged at said proximal portion of said shaft, a shaft rotating device, said shaft rotating device comprising an operating element for rotating said shaft, which is arranged at a proximal portion of said shaft and which is in driving connection with said shaft such that said shaft is rotatable relative to said handle against frictional forces, a frictional element having a first surface, wherein said first surface of said frictional element is in frictional contact with a second surface of a counterpart for keeping said shaft and said handle rotationally stationary with respect to each other and movable against said frictional forces, said operating element and said frictional element being in operational connection with respect to one another such that a torque applied to said operating element decreases said frictional forces, and said shaft and said frictional element being in operational connection with one another such that a torque applied to a distal portion of said shaft increases said frictional forces.

* * * * *